(12) United States Patent
Gebauer et al.

(10) Patent No.: US 10,450,540 B2
(45) Date of Patent: Oct. 22, 2019

(54) BAG ASSEMBLY FOR CULTIVATION OF CELLS

(71) Applicant: GE Healthcare Bio-Sciences AB, Uppsala (SE)

(72) Inventors: Klaus Gebauer, Uppsala (SE); Andreas Castan, Uppsala (SE); Camilla Estmer-Nilsson, Uppsala (SE); Thomas Falkman, Uppsala (SE); Anders Wilen, Uppsala (SE); Michael Miller, Westborough, MA (US); Ralph Stankowski, Westborough, MA (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 77 days.

(21) Appl. No.: 15/306,691

(22) PCT Filed: Apr. 27, 2015

(86) PCT No.: PCT/EP2015/059054
§ 371 (c)(1),
(2) Date: Oct. 25, 2016

(87) PCT Pub. No.: WO2015/180908
PCT Pub. Date: Dec. 3, 2015

(65) Prior Publication Data
US 2017/0044477 A1 Feb. 16, 2017

Related U.S. Application Data

(60) Provisional application No. 62/003,754, filed on May 28, 2014.

(51) Int. Cl.
| C12M 1/00 | (2006.01) |
|---|---|
| C12M 3/06 | (2006.01) |
| C12M 1/02 | (2006.01) |
| C12Q 3/00 | (2006.01) |

(52) U.S. Cl.
CPC ............ *C12M 23/14* (2013.01); *C12M 23/26* (2013.01); *C12M 23/34* (2013.01); *C12M 23/58* (2013.01); *C12M 27/16* (2013.01); *C12M 41/24* (2013.01); *C12Q 3/00* (2013.01)

(58) Field of Classification Search
None
See application file for complete search history.

(56) References Cited

U.S. PATENT DOCUMENTS

| 3,257,072 | A | 6/1966 | Reynolds |
|---|---|---|---|
| 5,017,490 | A | 5/1991 | Taiariol et al. |
| 6,190,913 | B1 | 2/2001 | Singh |
| 8,383,395 | B2 | 2/2013 | Hata et al. |
| 2009/0042293 | A1* | 2/2009 | Hata ............... C12M 23/58 435/383 |
| 2009/0111179 | A1* | 4/2009 | Hata ............... B01L 9/523 435/394 |
| 2011/0217690 | A1 | 9/2011 | Niazi |
| 2014/0315303 | A1 | 10/2014 | Huang |

FOREIGN PATENT DOCUMENTS

| DE | 19707497 A1 | 2/1998 |
|---|---|---|
| JP | 03505164 A | 11/1991 |
| JP | 2000503546 A | 3/2000 |
| JP | 2010136628 A | 6/2010 |
| WO | 90/10690 A1 | 9/1990 |
| WO | 9807828 A1 | 2/1998 |
| WO | 2007052716 A1 | 5/2007 |
| WO | 2008/101127 A2 | 8/2008 |
| WO | 2013086183 A1 | 6/2013 |

OTHER PUBLICATIONS

International Search Report and Written Opinion regarding International Application No. PCT/EP2015/059054, dated Sep. 17, 2015, 14 pages.
Japan Notice of Preliminary Rejection for Japanese Patent Application No. 2016-568628, dated Mar. 26, 2019, 6 pages.

* cited by examiner

*Primary Examiner* — Blaine Lankford
(74) *Attorney, Agent, or Firm* — Wood IP LLC (57) ABSTRACT

The invention discloses a flexible bag assembly for cultivation of cells, comprising one or more bags forming a plurality of cultivation compartments, wherein a drain port in at least a first cultivation compartment is adapted to be fluidically connected with a second cultivation compartment upon opening of a valve means. It also discloses a bioreactor with the bag assembly mounted on a rocking tray and a method of cultivating cells in the assembly.

38 Claims, 10 Drawing Sheets

BAG ASSEMBLY FOR CULTIVATION OF CELLS

CROSS-REFERENCE TO RELATED APPLICATIONS

This application is a filing under 35 U.S.C. 371 of international application number PCT/EP2015/059054, filed Apr. 27, 2015, which claims priority to U.S. application number 62/003,754, filed May 28, 2014, the entire disclosures of each of which are hereby incorporated by reference.

TECHNICAL FIELD OF THE INVENTION

The present invention relates to bioreactors for cell cultivation, and more particularly to flexible bag bioreactors suitable for multi-stage expansion of cell cultures, such as seed train expansion or expansion of cells for cell therapy. The invention also relates to a method of expanding cell cultures in flexible bag bioreactors.

BACKGROUND OF THE INVENTION

When cell cultures are scaled up from a small cell bank sample to larger production batches, this normally has to be made in several steps, using separate bioreactors. This sequence of cultivations is often called a seed train and is needed in order to keep the cell densities within a certain optimal window, often in the order of >$10^5$ cells per ml. In large scale production of biopharmaceuticals where the scale-up is from a small cryopreserved vial sample up to several $m^3$, the seed train can involve up to six steps and take several weeks. It is also a complex procedure in that sterile transfer of the culture from one bioreactor to another is needed, such that transfers have to be made in LAF benches or sterile cleanrooms. Even under these conditions there is also a certain risk for adventitious infections, which can have disastrous consequences for a high value large scale culture. Similar concerns apply also for expansion of cells, e.g. stem cells, to be used in clinical cell therapy.

With the general trend towards single-use vessels for cell culture, there is an increasing tendency towards using flexible bag bioreactors in seed trains. However, the need to empty one smaller bag and to transfer the content into a larger bag still remains and is a work-intensive operation with some risk of contamination. It has been suggested to gradually increase the culture volume in flexible bags either by clamping off part of the bag over the entire bag cross section and then removing the clamp (WO2008153401) or by starting with a folded bag and then unfolding it ((US20100055764). However, these solutions do not provide good sealing between the used and unused compartments, leading to leakage of culture into the unused compartments and contamination of the cell culture by substances released from cells grown under unsuitable conditions. These methods also involve a substantial risk of mechanical damage to the bags, with resulting risks of bag rupture.

Accordingly there is a need for a safe and convenient way of transferring cell cultures from one flexible culture compartment to another under sterile conditions. There is also a need for accurate temperature control of sensitive cell cultures, particularly in small volumes.

SUMMARY OF THE INVENTION

One aspect of the invention is to provide a flexible bag assembly which allows transfer of a cell culture from one cultivation compartment to another without risk of premature leakage between compartments or of bag damage. This is achieved with an assembly as defined in claim 1.

One advantage is that the cultivation compartments can be conveniently placed on a single tray and agitated using the same agitation means. A further advantage is that the culture can be easily transferred using e.g. gravity or gas pressure.

A second aspect of the invention is to provide a bioreactor assembly with flexible bags on a rocking platform, which allows transfer of a cell culture from one cultivation compartment to another without risk of premature leakage between compartments or of bag damage. This is achieved with an assembly as defined in the claims.

A third aspect of the invention is to provide a cultivation method where a cell culture is safely and conveniently transferred from one cultivation compartment to another. This is achieved with a method as defined in the claims.

A fourth aspect of the invention is to provide a flexible bag assembly which allows cultivation of cells in at least one cultivation compartment at substantially constant temperature. This is achieved with an assembly as defined in the claims.

A fifth aspect of the invention is to provide a bioreactor assembly which allows cultivation of cells in at least one cultivation compartment at substantially constant temperature. This is achieved with an assembly as defined in the claims.

A sixth aspect of the invention is to provide a cultivation method, where cells are cultivated at substantially constant temperature. This is achieved with a method as defined in the claims. Further suitable embodiments of the invention are described in the dependent claims.

DETAILED DESCRIPTION OF EMBODIMENTS

Figure 6:
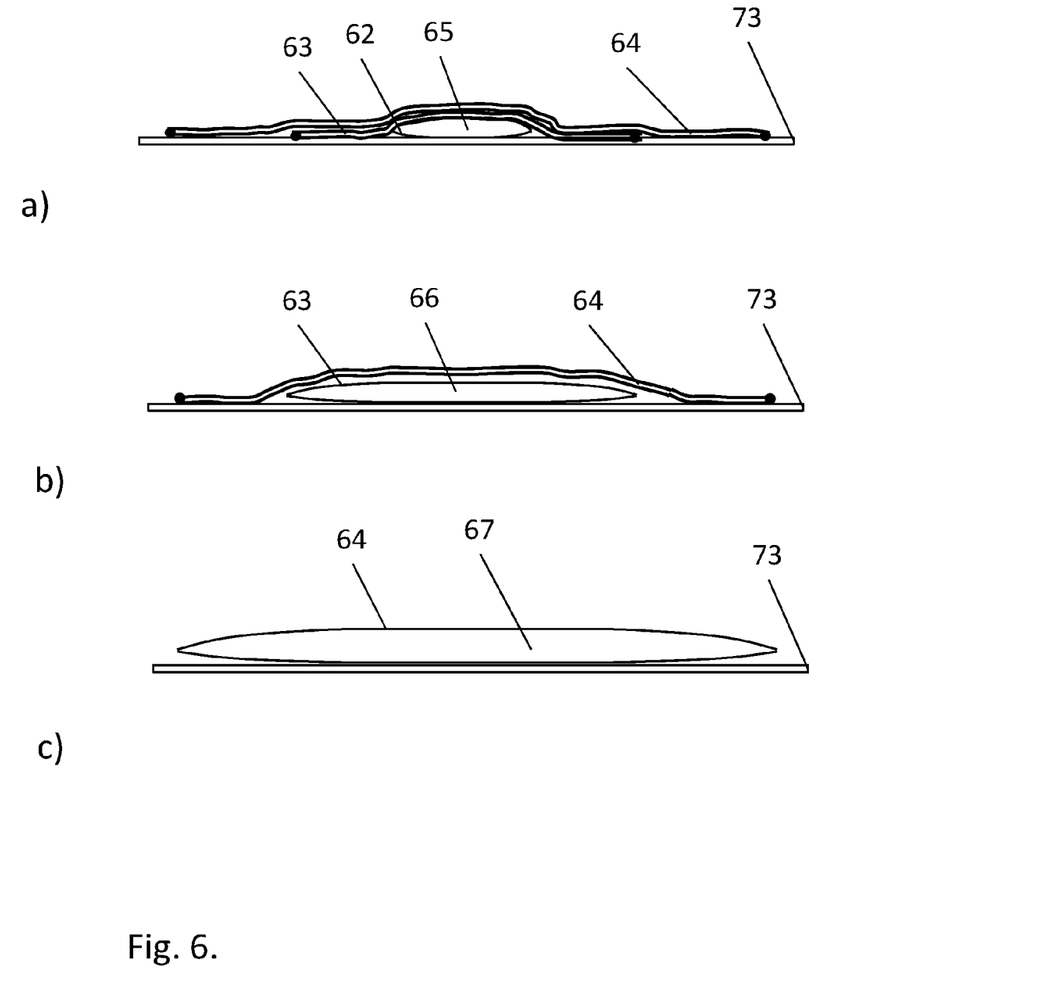
FIGS. 6A, 6B and 6C show an alternative sequence to FIG. 5, where the spent bag is removed before cultivation in the next bag. a) cultivation in a first bag, b) cultivation in a second bag and c) cultivation in a third bag.
Figure 7:
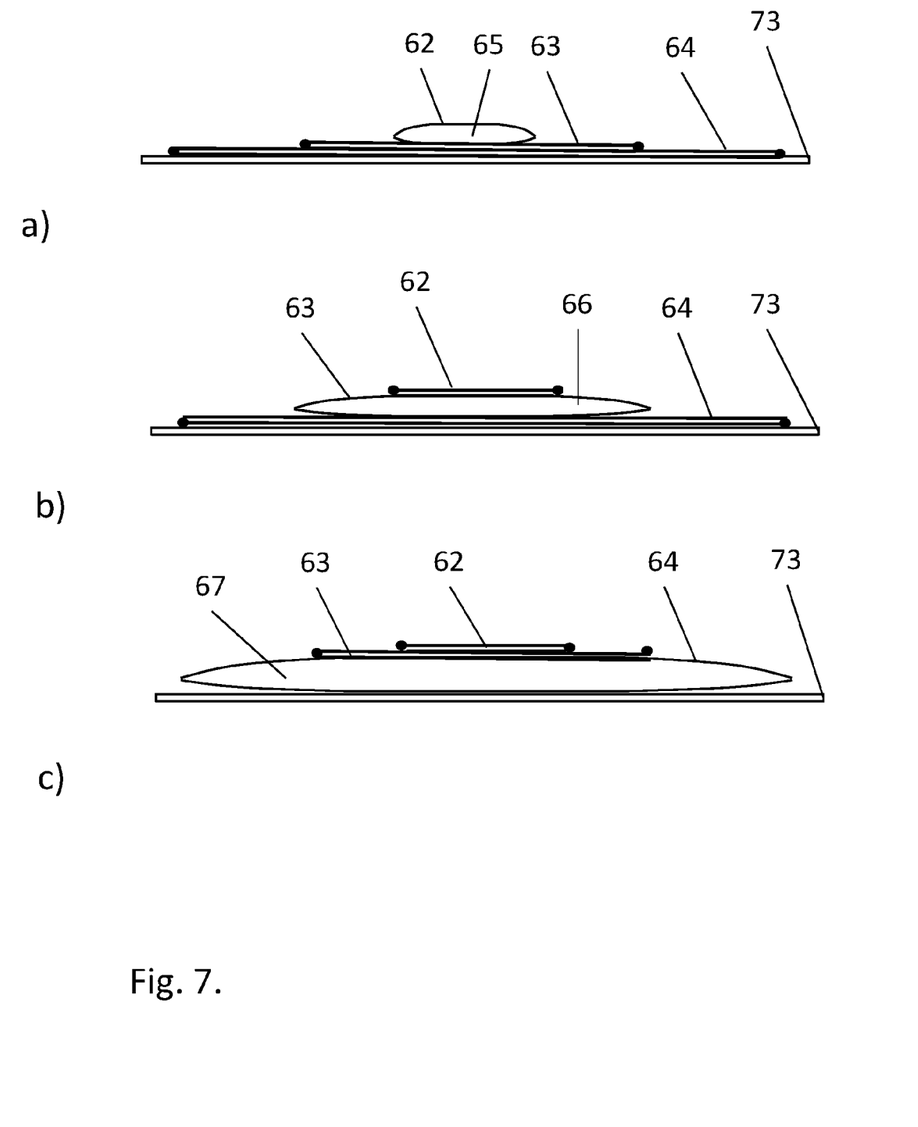
FIGS. 7A, 7B and 7C show an alternative stacked bag arrangement with the first bag at the top of the stack. a) cultivation in a first bag, b) cultivation in a second bag and c) cultivation in a third bag.
Figure 8:
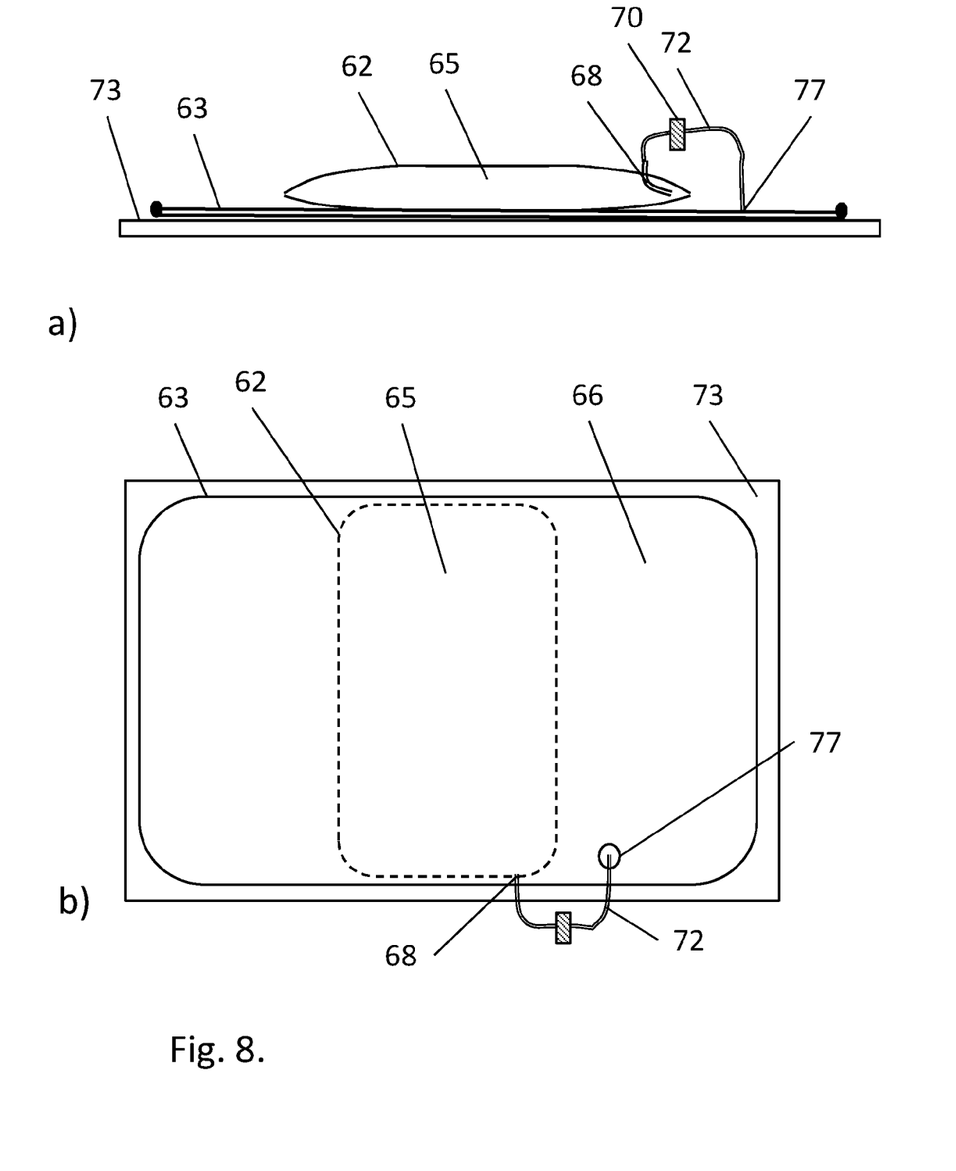
FIGS. 8A and 8B show two examples of the bag-to-bag connection. a) dip tube drain port in a first bag connected with an inlet port in a second bag via tubing in a loop above the stack, b) drain port in a first bag connected with an inlet port in a second bag via tubing in a loop outside the stack.
Figure 9:
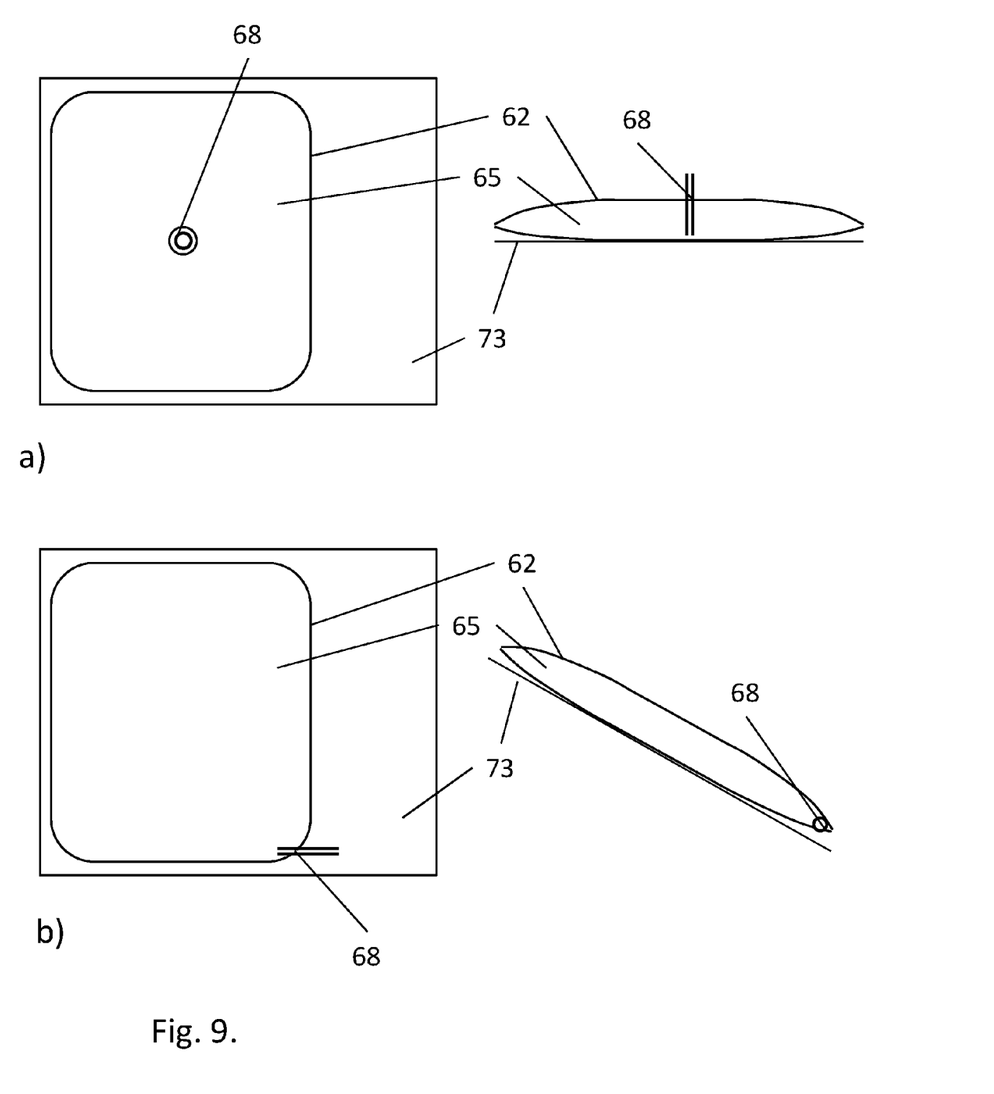
FIGS. 9A and 9B show two examples of drain ports: a) a dip tube used with a bag in horizontal position and b) a port used with a bag in inclined position.

In one aspect, illustrated by FIGS. 1-10, the present invention discloses a flexible bag assembly 1;21;41;61;81 for cultivation of cells. The assembly comprises one or more bags 2,3,4;22;42;62,63,64,82, such as one or more flexible and/or collapsible bags, which form a plurality of cultivation compartments 5,6,7;25,26,27;45,46,47;65,66,67;85,86,87, such as two, three or more compartments. A first drain port 8;28;48;68;88 in at least a first cultivation compartment 5;25;45;65;85 is adapted to be fluidically connected with a second cultivation compartment 6;26;46;66;86 upon opening of a first valve means 10;30;50;70;90. The second cultivation compartment may be larger than the first cultivation compartment, e.g. having a volume of at least 120%, such as at least 150% or 120-1000% of the volume of the first cultivation compartment. The drain port can suitably be located at a low point of the first cultivation compartment to facilitate complete draining of the compartment. A low point can here mean a point which is located within the lowermost 20%, 10% or 5% of the compartment volume, either when the compartment is in a cultivation position or when it is moved to a transfer or drainage position. Two examples of drain ports are shown in FIG. 9, with FIG. 9 a) showing a dip tube 68 that can be used with a bag in cultivation position and FIG. 9 b) showing a plain port 68 at the end of a bag, which is suitable for draining when the bag is in an inclined or vertical drainage position with the port at the lower end of the bag. As shown in FIG. 8 a), it is also possible to use a dip tube at the end of the bag as a drain port. This arrangement allows draining in both horizontal and inclined/vertical positions. The valve means can be in a closed position when cells are cultured in the first cultivation compartment and then moved/rearranged to an open position when the culture is to be transferred to the second compartment. It can then optionally be moved/rearranged to a closed position to prevent leakage back to the first compartment during cultivation in the second cultivation compartment. Alternatively, the valve means may also comprise a check valve (not shown), only allowing flow in the direction from the first to the second compartment. The valve means can be a valve, such as e.g. a pinch valve, a diaphragm valve, a disc valve, a ball valve, a gate valve, a needle valve or a piston valve but it can also be a clamp, e.g. a pinch clamp, or it can be a breakable closure, e.g. a rupture disc or a breakable weld between the compartments. The valve means can be reversible, i.e. it can be moved/rearranged back to a closed position from an open position or it can be irreversible, i.e. it can only be moved/rearranged from a closed position to an open position. Valves and clamps are examples of reversible valve means and breakable closures of irreversible valve means. Pinch valves and pinch clamps have an advantage from a sterility/contamination point of view in that they can be applied externally on tubing or conduits and do not have any wetted parts. Pinch valves or pinch clamps adapted for application on tubing or conduits of up to 10 mm inner diameter or up to 15 mm outer diameter are particularly suitable in that they are simple low cost components that provide efficient closure and opening. The function of the valve means is to prevent any leakage of the culture into the second compartment during cultivation in the first compartment, when in the closed position, and to allow easy flow from the first to the second compartment when in the open position. If the valve means is reversible, or comprises a check valve, the valve may also have a function of preventing backflow of the culture into the first compartment during cultivation in the second compartment, if so desired.

The bag(s) 2,3,4;22;42;62,63,64,82 may be manufactured from one or more flexible plastic films or laminates, joined and sealed e.g. by welding. The films/laminates may comprise polyolefins, such as e.g. polyethylenes and/or ethylene vinyl acetate copolymers, but also barrier layers, e.g. ethylene vinyl alcohol polymers and/or tear resistant layers of e.g. polyamides. The thickness of the films or laminates may e.g. be 50-300 micrometers, such as 100-250 micrometers.

The bag assembly of the invention can conveniently be arranged on a rocking tray 13;33;73;93 platform to provide agitation during cultivation. The tray can rock back and forth around an axis 16;36;76,96, e.g. placed somewhat below the tray. Rocking tray platforms suitable for this purpose are described e.g. in U.S. Pat. No. 6,190,913, which is hereby incorporated by reference in its entirety, and are commercially available as WAVE Bioreactor™ from GE Healthcare Bio-Sciences.

In certain embodiments, the flexible bag assembly 1;21;41;61;81 comprises at least three cultivation compartments and has a second drain port 9;29;49;89 in the second cultivation compartment 6;26;46;66;86, which is adapted to be fluidically connected with a third cultivation compartment 7;27;47;67;87 upon opening of a second valve means 11;31;51,91. The second drain port and the second valve means can be constructed as described above for the first drain port and first valve means. The third cultivation compartment may be larger than the second cultivation compartment, e.g. having a volume of at least 120%, such as at least 150% or 120-1000% of the volume of the second cultivation compartment, and/or at least 140%, such as at least 200% or 140-10 000% of the volume of the first cultivation compartment. This allows a safe and convenient three-step scale-up from the first, to the second and then to the third cultivation compartment.

Figure 1:
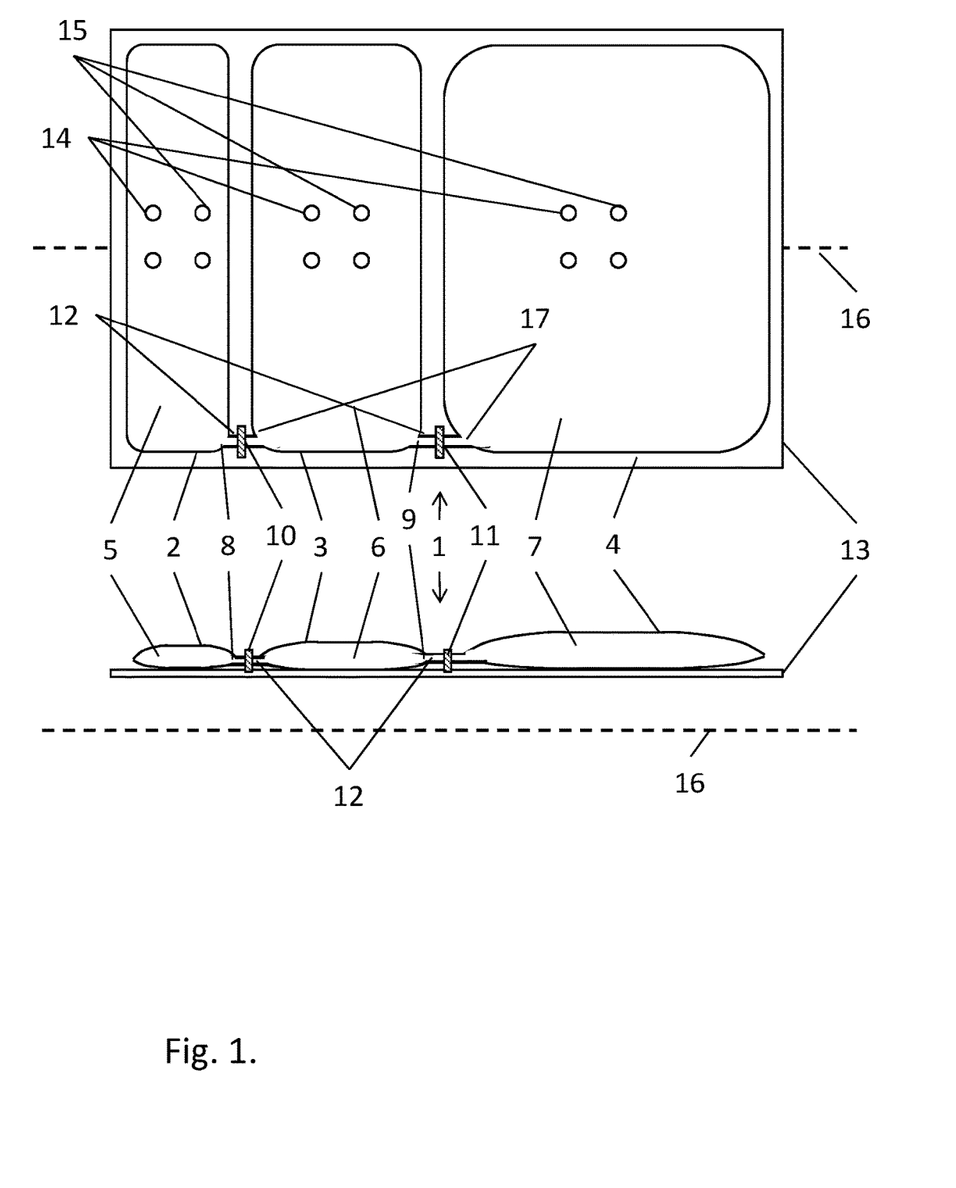
FIG. 1 shows an embodiment of the invention with three connectable bags arranged side by side on a tray.
Figure 4:
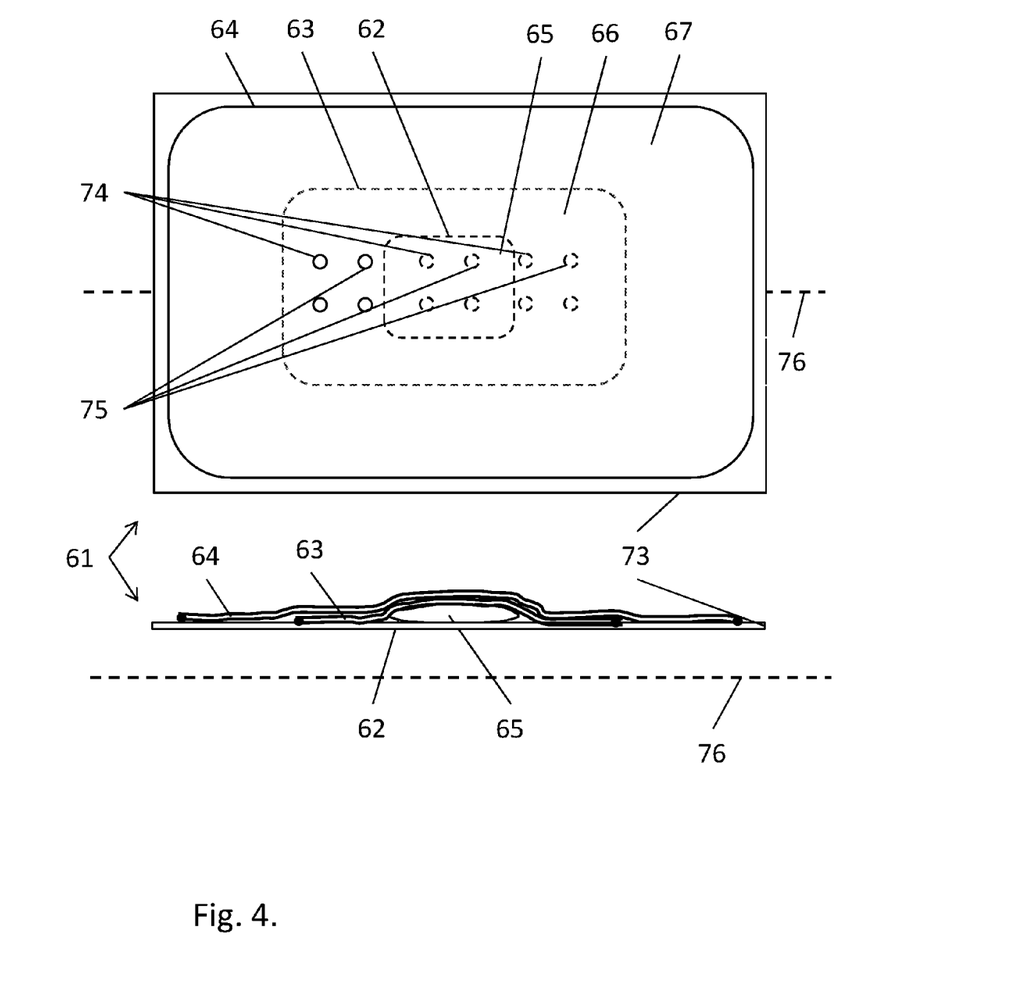
FIG. 4 shows an embodiment of the invention with three connectable bags stacked on a tray.
Figure 5:
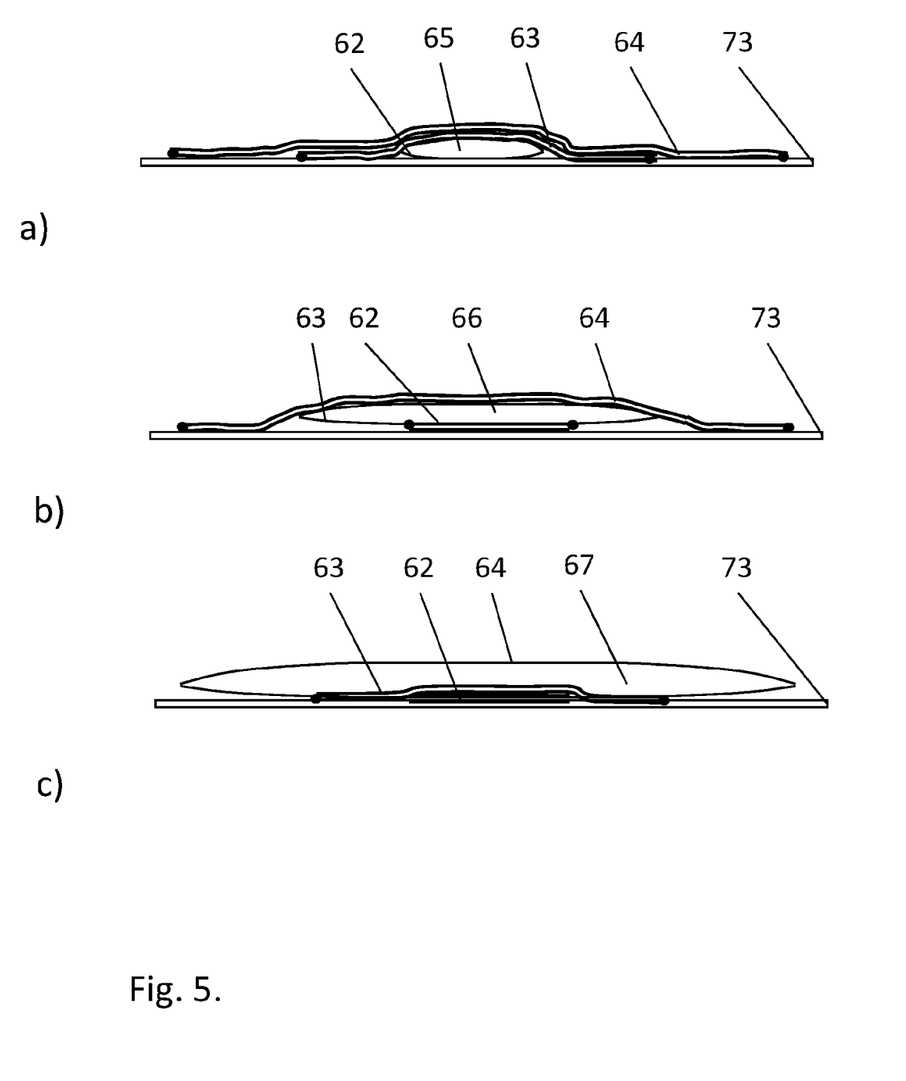
FIGS. 5A, 5B and 5C show a sequence of cultivations in the three bags of FIG. 4, starting in a first bag at the bottom of the stack. a) cultivation in a first bag, b) cultivation in a second bag and c) cultivation in a third bag.

In some embodiments, illustrated by FIGS. 1 and 4, the flexible bag assembly 1;61 comprises at least two bags, which are suitably connected by tubing 12. The tubing can be connected to a drain port 8,9 in a first bag and to a culture inlet 17 in a second bag. The valve means 10,11 may be a) valve components connected via the tubing, b) valves integrated with the tubing or c) externally applied devices such as pinch clamps or pinch valves. All these valve means are capable of preventing leakage in a closed position and allowing flow in an open position. The bags can be adapted to be placed beside each other on a tray 13 as in FIG. 1 or they can be adapted to be stacked on top of each other on a tray 73 as in FIGS. 4-7. It is also possible to have a combination of bags placed beside each other and stacked on top of each other, e.g. with two or three bags beside each other as in FIG. 1 and one larger bag placed below or on top of the two or three bags. The arrangement beside each other has the advantage that the assembly is easily prepared and arranged on the tray and the operation is simple. The stacked arrangement has the advantage that the tray area is more efficiently used. When bags are stacked, it is advantageous if the connections are made by tubing and the tubing extends in a loop outside or above the stack. This improves accessibility and allows for easy operation of the valve means if it is placed in the loop. The bags can e.g. be stacked as shown in FIGS. 5 and 6, with the second bag on top of the first bag and optionally a third bag (and further bags) on top of the second bag. This arrangement has the advantage that any sensors at the bottom side of the bags can be in contact with sensor contacts on the tray surface. In particular, a culture sequence as illustrated in FIG. 6, where the first bag is removed from the stack after transfer of the culture to the second bag and the second bag is optionally removed after transfer of the culture to a third bag, allows sensors in all the bags to be in contact with the same sensor contacts on the tray surface. This sequence also has the advantage that during cultivation the entire bag area is in contact with the tray surface, which facilitates heat transfer from a heating element located on the tray surface and improves the temperature control. Alternatively, the bags can be stacked as shown in FIG. 7, with the second bag below the first bag and optionally a third bag (and further bags) below the second bag. This arrangement allows for easier constriction of the connections, as the drain port of a previous bag can easily be connected to an inlet port on the free top surface of a subsequent bag via a tubing loop above the stack. Another advantage is that it is easier to remove samples from each bag from sample ports on the free top surfaces of the bags. If needed, sheet-formed heating elements may be interspersed with the bags in the stack to improve the temperature control. For all the stack arrangements, if a spent bag is to be removed from the stack after transfer of the culture to a subsequent bag, this can easily be done under maintained sterile conditions e.g. by hot sealing disconnection if the connecting tubing is thermoplastic (made from e.g. soft PVC or thermoelastomers). Equipment for hot sealing of thermoplastic tubing is readily available, e.g. under the name of Hot Lips Tube Sealer (GE Healthcare Bio-Sciences AB).

Figure 2:
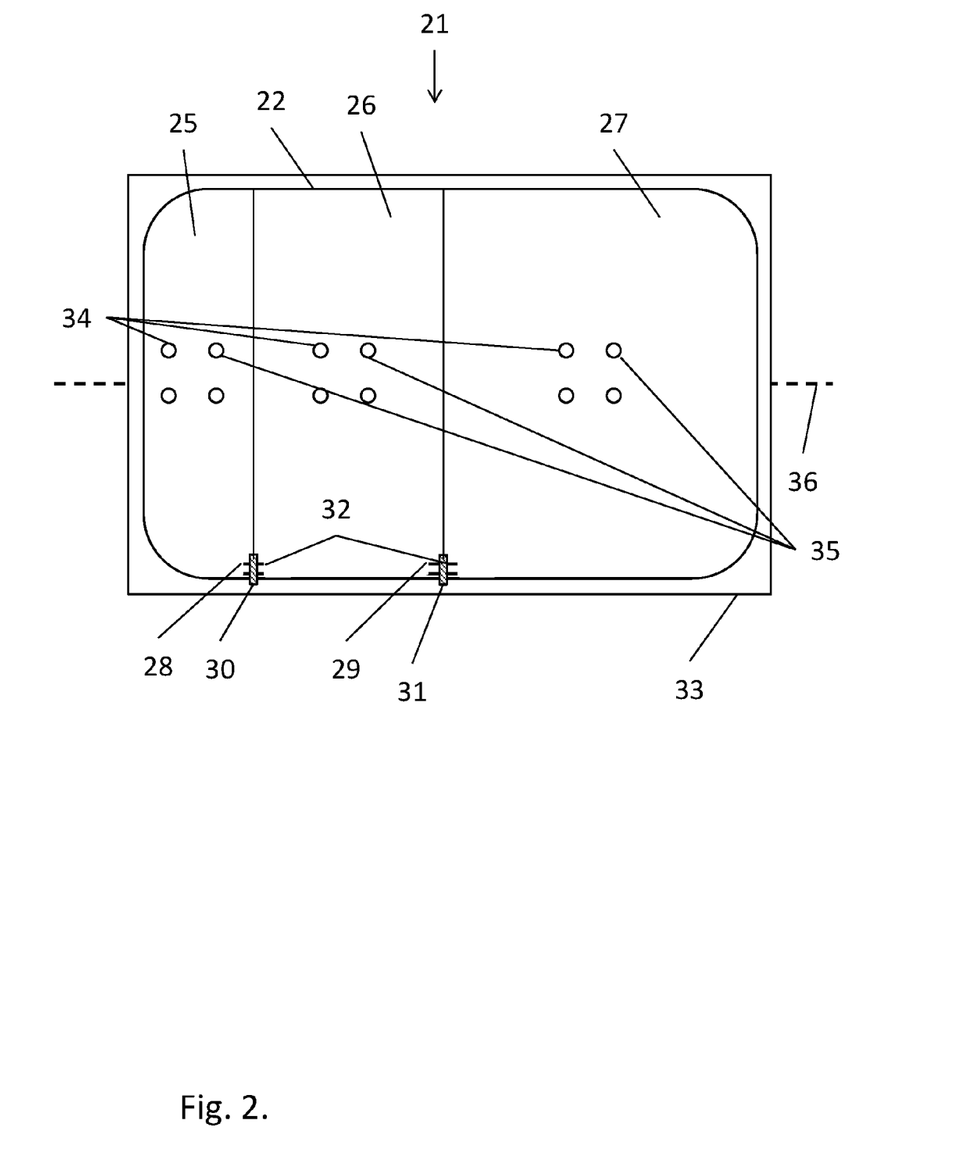
FIG. 2 shows an embodiment of the invention with one bag having three connectable cultivation compartments.
Figure 3:
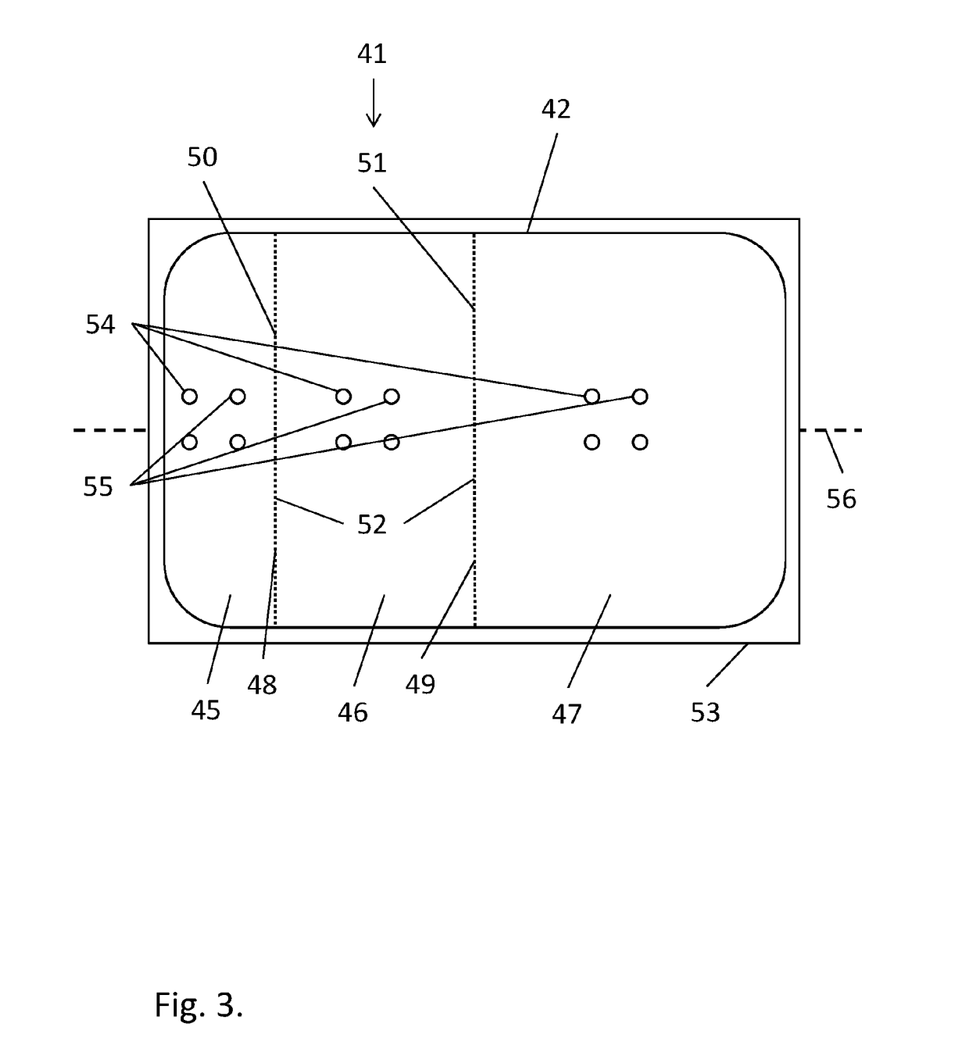
FIG. 3 shows another embodiment of the invention with one bag having three connectable cultivation compartments.
Figure 10:
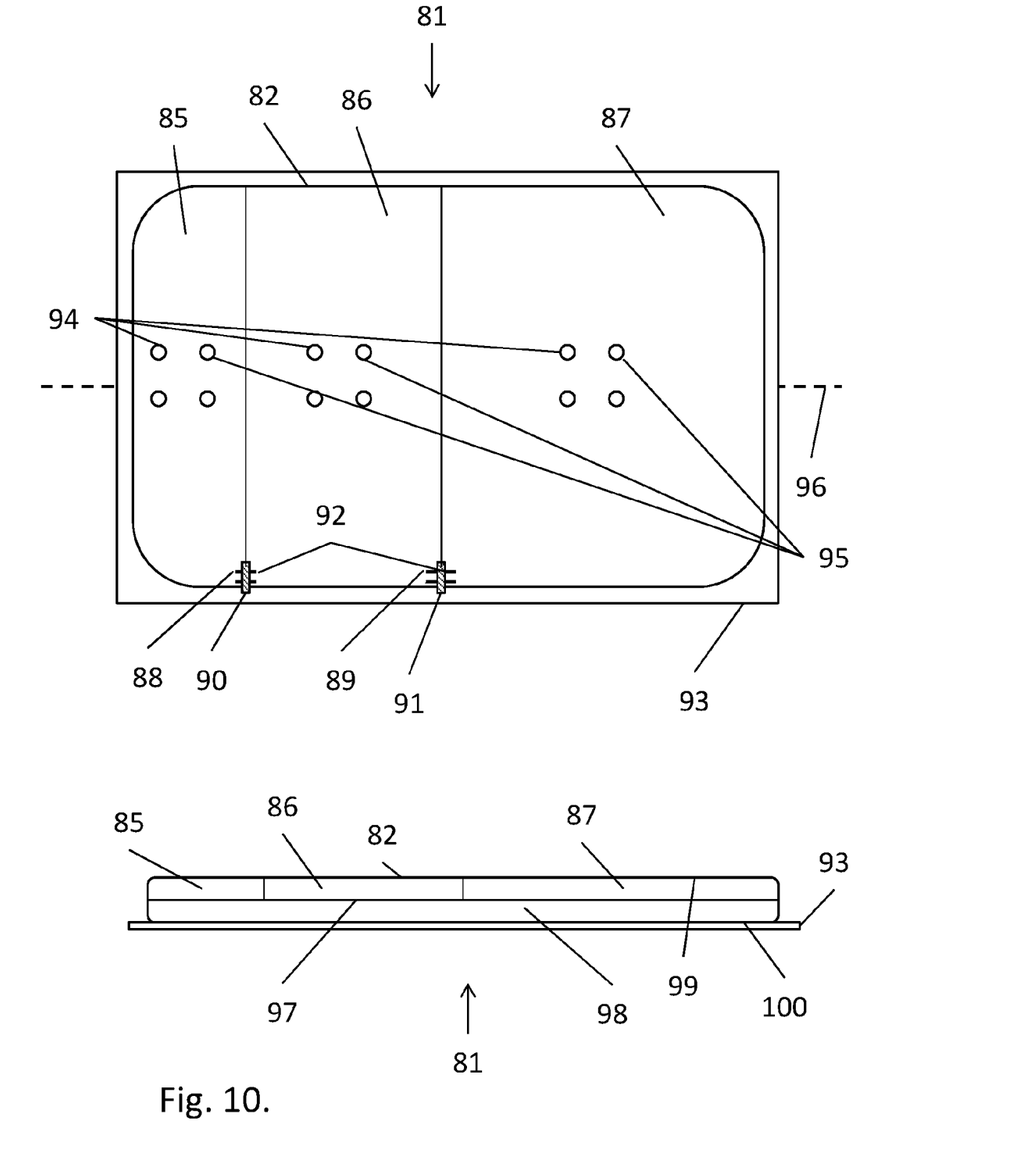
FIG. 10 shows an embodiment of the invention with one bag having three connectable cultivation compartments and a temperature control compartment.

In certain embodiments, illustrated by FIGS. 2-3 and 10, the flexible bag assembly 21;41 comprises at least one multi-compartment bag 22;42;82 with cultivation compartments 25,26,27;45,46,47;85,86,87 connected or connectable via internal conduits 32;92. The internal conduits can suitably have internal (circle-equivalent) diameters measuring less than 10%, such as less than 5%, of the cross section of the bag. As shown in FIGS. 2 and 10, the compartments may be delimited from each other by e.g. walls or welded seams extending at least over a major part of the bag cross section, such as the entire cross section. The internal conduits 32;92 can then e.g. be the hollow portions of ports 28,29;88,89 in walls or short pieces of tubing inserted as ports 28,29;88,89 in weld seams. The valve means 30,31;90,91 can either be integrated in the conduits or applied externally as clamps or pinch valves. The internal conduits 32;92 may alternatively be parts of the bag cross section to which the walls or weld seams do not extend, i.e. the walls/weld seams only extend over a part of the bag cross section, such as over 90-99.9% or 95-99.5% of the bag cross section, leaving the remaining part of the cross section open to form the internal conduits 32;92. The valve means can in this case suitably be externally applied clamps, which can provide leak-free seals as they only have to be applied over a short distance.

In certain embodiments, illustrated by FIG. 10, the flexible bag assembly 81 further comprises at least one bag 82 with at least one temperature control compartment 98. The bag 82 can suitably comprise a top film 99, a bottom film 100 and a delimiting film 97, wherein the delimiting film delimits the temperature control compartment 98 from the cultivation compartments 85,86,87. The temperature control compartment can suitably comprise at least an inlet (not shown) for a thermostating fluid. It may further comprise an outlet (not shown) for the thermostating fluid. The thermostating fluid can e.g. be water or cell culture medium. The thermostating fluid, such as water, can be circulated through the temperature control compartment via the inlet and outlet from/to a thermostating appliance, e.g. a thermostate bath. Alternatively, the temperature control compartment may be adapted to be located in direct contact with at least one temperature control surface or heating element on the tray 93. In this case, the thermostating fluid, such as water or cell culture medium, need not be circulated but can act as a temperature buffer. If the temperature control fluid is cell culture medium, the temperature control compartment may be fluidically connectable to the first, second or third cultivation compartment via a drain port and a valve means (not shown) and can then be used as a further cultivation compartment in the same way as discussed above. The advantage of having a temperature control compartment is that, particularly in small cultivation compartments, the temperature may be difficult to control accurately enough by the conventional means of having a temperature sensor in the cultivation compartment and controlling the temperature with a temperature control (heating) surface on the tray using a feedback loop. With a temperature control compartment a better temperature stability can be obtained due to the heat capacity of the thermostating fluid. The effect of the temperature control compartment is most evident for cultivation compartments of volumes 1 L or less such as 250 mL or less, 100 ml or less, 50-100 mL, 50-250 mL or 50-100 mL. This applies in particular to the first cultivation compartment. The volume of the temperature control compartment may e.g. be at least 1L, such as at least 2L or at least 5 L or at least 10 times, such as at least 20 times the volume of the first cultivation compartment.

In some embodiments, illustrated by FIG. 3, the flexible bag assembly 41 comprises at least one multi-compartment bag 42 with cultivation compartments 45,46,47 connectable via at least one breakable seal 52. The breakable seal may e.g. be a weak weld, as disclosed in EP 2,226,058A1 or U.S. Pat. No. 4,519,499, which are hereby incorporated by reference in their entireties. The breakable seal can e.g. constitute the entire delimitation between two adjacent compartments. In this case the weld is broken by bursting or other mechanical action from the outside of the bag, such that a first compartment opens up into a second compartment and the second cultivation step is conducted in the joint compartment. An advantage of this arrangement is that no extra components are needed. A further advantage is that, although separate gas inlets 54 and outlets 55 for each compartment are shown in FIG. 3, the cultivation can be performed with only one gas inlet and one gas outlet for the entire bag with all the compartments.

In certain embodiments of the flexible bag assembly, each cultivation compartment comprises a gas inlet 14;34;54;74; 94 and a gas outlet 15;35;55;75;95. These inlets and outlets may be equipped with sterile filters (not shown) to prevent infection/contamination of the culture and are used to supply e.g. air/oxygen to the culture and to remove gaseous metabolites, such as carbon dioxide. They can also be used to supply a gas pressure to transfer the culture liquid from one compartment to another. The gas may e.g. be supplied via a gas inlet, while either closing the gas outlet or simply relying on the outlet sterile filter to provide a sufficiently high back pressure for transport of the liquid. The cultivation compartment(s) may also comprise one or more of sampling outlets, inlets for culture medium and sensors for e.g. temperature, cell density, pH and concentrations of e.g. oxygen or metabolites.

The bag assemblies disclosed above can suitably be supplied preassembled and presterilized, such as by radiation sterilization, e.g. by gamma or electron beam irradiation. Suitably, all liquid-contact materials are selected to be radiation-stable and to give low levels of leachables also after irradiation. All materials can e.g. be of USP VI quality.

In a second aspect, illustrated by FIGS. 1-4, the invention discloses a bioreactor assembly, comprising the flexible bag assembly 1;21;41;61;81 as disclosed above mounted on a tray 13;33;53;73;93 adapted to rock back and forth around at least one axis 16;36;56;76;96. The rocking mechanism and the support for the tray are not shown in the figures, but are described in detail in U.S. Pat. No. 6,190,913 and V Singh: Cytotechnology 30(1-3), 149-158 (1999). The bioreactor may further comprise a cell culture in at least one of the cultivation compartments 5,6,7;25,26,27;45,46,47;65, 66,67;85,86,87. The tray may be equipped with a temperature control (heating) surface in direct contact with at least one bag. It may further be equipped with sensor connectors in electrical contact with at least one bag. At least one of the cultivation compartments may be connected to a gas supply via a gas inlet and a sterile filter.

In a third aspect the present invention discloses a method of cultivating cells. The method comprises the steps of:

a) providing the bioreactor as disclosed above;
b) introducing culture media and cells in the first cultivation compartment 5;25;45;65;85;
c) cultivating the cells in the first cultivation compartment to provide a first cell culture;
d) opening a first valve means 10;30;50;70;90 to fluidically connect the first cultivation compartment with the second cultivation compartment 6;26;46;66;86;
e) transferring the first cell culture to the second cultivation compartment;
f) introducing culture media to the second cultivation compartment, and;
g) cultivating the cells in the second cultivation compartment to provide a second cell culture.

The cultivations in the first and second cultivation compartments can be made using methods well known in the art and described e.g. in V Singh: Cytotechnology 30(1-3), 149-158 (1999) or Clincke et al., Biotechnol. Prog., 2013, Vol. 29, No. 3. Air or other gases may be supplied via gas inlets 14;34;74;94 and excess air/gas together with gaseous metabolites (e.g. carbon dioxide) may be vented via gas outlets 15;35;75;95. The cultivation in the first compartment may be continued until a predetermined viable cell density (VCD) is reached, e.g. $1.0 \times 10^5$, $2.0 \times 10^5$, $5.0 \times 10^5$ or $1.0 \times 10^6$ viable cells/ml. The VCD may e.g. be measured with an inline biomass sensor, e.g. as described in U.S. Pat. No. 8,180,575 or WO 2010/010313A2, which are hereby incorporated by reference in their entireties. When the predetermined VCD has been reached, steps d) and further may be initiated. The transfer in step e) may be accomplished by gravity, e.g. by inclining the tray with the bags or raising it vertically. It may also be accomplished by gas pressure, suitable delivered via the gas inlet of the first bag, in which case the back pressure of a sterile filter on the gas outlet may be sufficient to allow the transfer. The transfer may further be accomplished by other means, e.g. application of pressure on the first or by combinations of different means.

In some embodiments the method further comprises a step e'), after step e), of closing the first valve means. Alternatively, or additionally, the first and second compartments may be disconnected from each other e.g. by cutting and sealing any tubing 12;72 between the compartments. In the case where the compartments are located in separate bags, this enables removal of the first bag from the tray, which can improve heat transfer and/or allow contact with sensor contacts on the tray surface as discussed above.

In certain embodiments the method further comprises the steps of:

h) opening a second valve means to fluidically connect the second cultivation compartment with the third cultivation compartment;
i) transferring the second cell culture to the third cultivation compartment;
j) introducing media to the third cultivation compartment, and;
k) cultivating the cells in the third cultivation compartment to provide a third cell culture.

This method can further comprise a step i'), after step i), of closing the second valve means. Alternatively, or additionally, the second and third compartments may be disconnected from each other e.g. by cutting and sealing any tubing 12;72 between the compartments.

In some embodiments, step k) and/or g) may be conducted in perfusion mode, i.e. by conveying at least part of the culture to a filter where a filtrate is removed and conveying the cells back to the culture and replacing the removed filtrate with fresh culture medium. This allows for further increases in the VCD.

In a fourth aspect the present invention discloses a flexible bag assembly for cultivation of cells. The assembly comprises at least one bag 82 with at least one cultivation compartment 85,86,87 and at least one temperature control compartment 98. The temperature control compartment can suitably be adapted to rest on a tray support, with the cultivation compartment(s) above the temperature control compartment. The cultivation compartment(s) may be fluidically connectable as disclosed above, but they may also be separate and adapted for parallel cultivation. The bag 82 can, as illustrated by FIG. 10, comprise a top film 99, a bottom film 100 and a delimiting film 97, wherein the delimiting film delimits the at least one temperature control compartment 98 from at least one cultivation compartment 85,86,87, such as each cultivation compartment. The cultivation compartment(s), such as each cultivation compartment, may e.g. have a volume of less than 1L, such as 50-250 mL, and/or the volume of said temperature control compartment may e.g. be at least 10 times the volume of at least one cultivation compartment, such as of each cultivation compartment. The temperature control compartment may e.g. comprise an inlet and an outlet for a thermostating fluid to allow for circulation of thermostating fluid from e.g. a thermostat bath. Alternatively the temperature control compartment may have an inlet for thermostating fluid to allow for cultivation under conditions where the temperature control compartment is closed and acts as a temperature buffer.

In a fifth aspect the present invention discloses a bioreactor assembly comprising:

a) at least one bag 82 or bottle with at least one cultivation compartment 85,86,87;
b) at least one flexible temperature control compartment 98 comprising a thermostating fluid, and;
c) a tray 93 or a stack of trays adapted to rock back and forth around at least one axis 96.

The at least one flexible temperature control compartment is mounted or placed on the tray and the at least one bag or bottle is suitably located on top of the at least one flexible temperature control compartment. Thus, the heat transfer between the thermostating fluid and a cell culture in the cultivation compartment can proceed efficiently and the heat capacity of the thermostating fluid provides good temperature control within a narrow temperature range even for small cultivation compartments, such as cultivation compartments of volumes 1 L or less such as 250 mL or less, 100 ml or less, 50-100 mL, 50-250 mL or 50-100 mL. The bag 82 may comprise e.g. one, two, three, four, five, six, seven, eight, nine or ten cultivation compartments, which can be adapted for parallel cultivation and/or for sequential cultivation as disclosed above. The flexible temperature control compartment may form a part of the at least one bag 82, i.e. bag 82 may comprise both the flexible temperature control compartment 98 and at least one cultivation compartment 85,86,87, e.g. as illustrated in FIG. 10. The at least one bag may further comprise a top film 99, a bottom film 100 and a delimiting film 97, wherein the delimiting film delimits the at least one temperature control compartment 98 from at least one cultivation compartments 85,86,87. With this arrangement, an integral bag with one or more cultivation compartments in a top part of the bag and a temperature control compartment in a bottom part is obtained. The temperature control compartment can be equipped with an inlet and an outlet for thermostating fluid to allow circulation of the fluid from e.g. a thermostat bath through the temperature control compartment. One or more of the cultivation compartments, such as each cultivation compartment, may also be equipped with temperature sensors, which can be electrically or electromagnetically connected to a control unit to allow temperature control with a feedback loop. The control unit can further be connected to a thermostat bath or other temperature control equipment in a feedback loop. Further, or alternatively, the temperature control compartment may comprise a temperature sensor, which can be connected to the control unit. The tray may be equipped with a temperature control (heating) surface in direct contact with at least one bag. It may further be equipped with sensor connectors in electrical contact with at least one bag. At least one of the cultivation compartments may be connected to a gas supply via a gas inlet and a sterile filter.

In a sixth aspect the present invention discloses a method of cultivating cells. The method comprises the steps of:
a) providing the bioreactor assembly as disclosed above;
b) introducing culture media and cells in at least one cultivation compartment 85,86,87 and;
d) cultivating the cells in the at least one cultivation compartment.

In certain embodiments, the temperature in step c) is maintained within a range of a target temperature +/−2° C., such as +/−1° C. or +/−0.5° C. The target temperature can depend on the cell type, and can for mammalian cells be e.g. 35-38° C., such as 36-37° C.

In some embodiments, the thermostating fluid is circulated through said flexible temperature control compartment. This allows for precise control of the temperature. Alternatively, the temperature control compartment is in contact with a temperature control (heating) surface on the tray and the temperature is controlled using a temperature sensor in/on the temperature control compartment using a control unit and a feedback loop.

In certain embodiments said at least one cultivation compartment comprises a temperature sensor which is electrically or electromagnetically connected to a control unit and the temperature of said thermostating fluid and/or said cultivation compartment is controlled by the control unit using a feedback loop.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if individually incorporated.

The invention claimed is:

1. A flexible bag assembly for cultivation of cells in multi-stage expansion, comprising one or more bags forming a plurality of cultivation compartments of different sizes that are adapted for multi-stage cultivation stages respectively,
wherein a drain port in at least a first cultivation compartment is adapted to be fluidically connected with a second cultivation compartment upon opening of a valve means of the drain port to transfer the content of the first cultivation compartment to the second cultivation compartment upon completion of a first cell cultivation stage to leave the first cultivation compartment empty, and
wherein the drain port is closed during each stage of cell cultivation.

2. The flexible bag assembly of claim 1, wherein said second cultivation compartment has a volume of at least 120% of the volume of the first cultivation compartment.

3. The flexible bag assembly of claim 1, comprising at least three cultivation compartments and wherein a second drain port in the second cultivation compartment is adapted to be fluidically connected with a third cultivation compartment upon opening of a second valve means.

4. The flexible bag assembly of claim 3, wherein said third cultivation compartment has a volume of at least 120% of the volume of the second cultivation compartment.

5. The flexible bag assembly of claim 1, wherein the first cultivation compartment is a rigid or semirigid vessel.

6. The flexible bag assembly of claim 1, wherein said valve means is a valve or a clamp.

7. The flexible bag assembly of claim 6, wherein said valve means is a pinch valve or a pinch clamp.

8. The flexible bag assembly of claim 7, wherein said pinch valve or pinch clamp is adapted for application on tubing or conduits of up to 15 mm outer diameter.

9. The flexible bag assembly of claim 1, wherein at least one of said drain ports is a dip tube.

10. The flexible bag assembly of claim 1, comprising at least two bags connected by tubing.

11. The flexible bag assembly of claim 10, wherein said at least two bags are adapted to be placed beside each other on a tray.

12. The flexible bag assembly of claim 10, wherein said at least two bags are adapted to be stacked on a tray or a stack of trays.

13. The flexible bag assembly of claim 1, comprising at least one multicompartment bag with cultivation compartments connected or connectable via internal conduits.

14. The flexible bag assembly of claim 1, comprising at least one multicompartment bag with cultivation compartments connectable via at least one breakable seal.

15. The flexible bag assembly of claim 1, comprising at least one bag comprising at least one temperature control compartment.

16. The flexible bag assembly of claim 15, wherein said at least one bag comprises a top film, a bottom film and a delimiting film, wherein the delimiting film delimits the at least one temperature control compartment from at least said first cultivation compartment.

17. The flexible bag assembly of claim 16, wherein said temperature control compartment comprises a thermostating fluid inlet and optionally a thermostating fluid outlet.

18. The flexible bag assembly of claim 16, wherein the volume of said first cultivation compartment is less than 1 L and/or the volume of said temperature control compartment is at least 10 times the volume of said first cultivation compartment.

19. The flexible bag assembly of claim 1, adapted for cell cultivation on a rocking tray platform having a gas inlet and a gas outlet for each cultivation compartments.

20. The flexible bag assembly of claim 16, wherein each cultivation compartment comprises a top film and a bottom delimiting film, delimiting one temperature control compartment from said each cultivation compartment.

21. The flexible bag assembly of claim 1, supplied pre-sterilized by radiation sterilization.

22. A bioreactor assembly, comprising the flexible bag assembly of claim 1 mounted on a tray, or a stack of trays, adapted to rock back and forth around at least one axis.

23. The bioreactor assembly of claim 22, comprising a cell culture in at least one of said cultivation compartments.

24. A method of cultivating cells, comprising the steps of:
  a) providing the bioreactor assembly of claim 22;
  b) introducing culture media and cells in said first cultivation compartment;
  c) cultivating the cells in said first cultivation compartment to provide a first cell culture;
  d) opening a first valve means to fluidically connect said first cultivation compartment with said second cultivation compartment;
  e) transferring said first cell culture to said second cultivation compartment;
  f) introducing media to said second cultivation compartment, and;
  g) cultivating the cells in said second cultivation compartment to provide a second cell culture.

25. The method of claim 24, further comprising a step e'), after step e), of closing the first valve means.

26. The method of claim 25, further comprising the steps of:
  h) opening a second valve means to fluidically connect said second cultivation compartment with a third cultivation compartment;
  i) transferring said second cell culture to said third cultivation compartment;
  j) introducing media to said third cultivation compartment, and;
  k) cultivating the cells in said third cultivation compartment to provide a third cell culture.

27. The method of claim 26, further comprising a step i'), after step i), of closing said (second) valve means.

28. A flexible bag assembly for cultivation of cells in multi-stage expansion, comprising one or more bags forming a plurality of cultivation compartments of different sizes that are adapted for cell cultivation in multi-stages respectively,
  wherein a drain port in at least a first cultivation compartment is adapted to be fluidically connected with a second cultivation compartment upon opening of a valve means of the drain port to transfer the content of the first cultivation compartment to the second cultivation compartment upon completion of a first cell cultivation stage to leave the first cultivation compartment empty,
  wherein the drain port is closed during each stage of cell cultivation,
  wherein said second cultivation compartment has a volume of at least 150% volume of the first cultivation compartment, and
  wherein said valve means is a pinch valve or a pinch clamp adapted for application on tubing or conduits of up to 15 mm outer diameter.

29. The flexible bag assembly of claim 28, comprising at least three cultivation compartments and wherein a second drain port in the second cultivation compartment is adapted to be fluidically connected with a third cultivation compartment upon opening of a second valve means and wherein said third cultivation compartment has a volume of at least 150% of the volume of the second cultivation compartment.

30. The flexible bag assembly of claim 28, comprising at least two bags connected by tubing, wherein said at least two bags are adapted to be placed beside each other on a tray or to be stacked on a tray or a stack of trays.

31. The flexible bag assembly of claim 28, comprising at least one multicompartment bag with cultivation compartments connected or connectable via internal conduits and/or via at least one breakable seal.

32. A bioreactor assembly, comprising the flexible bag assembly of claim 28 mounted on a tray, or a stack of trays, adapted to rock back and forth around at least one axis.

33. The bioreactor assembly of claim 32, comprising a cell culture in at least one of said cultivation compartments.

34. A method of cultivating cells, comprising the steps of:
  a) providing the bioreactor assembly of claim 32;
  b) introducing culture media and cells in said first cultivation compartment;
  c) cultivating the cells in said first cultivation compartment to provide a first cell culture;
  d) opening a first valve means to fluidically connect said first cultivation compartment with said second cultivation compartment;
  e) transferring said first cell culture to said second cultivation compartment;
  f) introducing media to said second cultivation compartment, and;
  g) cultivating the cells in said second cultivation compartment to provide a second cell culture.

35. The method of claim 34, further comprising a step e'), after step e), of closing the first valve means.

36. The method of claim 35, further comprising the steps of:
  h) opening a second valve means to fluidically connect said second cultivation compartment with a third cultivation compartment;
  i) transferring said second cell culture to said third cultivation compartment;
  j) introducing media to said third cultivation compartment, and;
  k) cultivating the cells in said third cultivation compartment to provide a third cell culture.

37. The method of claim 36, further comprising a step i'), after step i), of closing said (second) valve means.

38. A flexible bag assembly for cultivation of cells adapted for cell cultivation in multi-stage expansion on a rocking tray platform, comprising one or more bags forming three cultivation compartments of different sizes that are adapted for multi-stages cell culture expansion respectively,
  wherein a drain port in a first cultivation compartment is adapted to be fluidically connected with a second cultivation compartment upon opening of a valve means of the drain port to transfer the content of the first cultivation compartment to the second cultivation compartment upon completion of a first cell cultivation stage to leave the first cultivation compartment empty and said second cultivation compartment has a volume of at least 150% volume of the first cultivation compartment,
wherein a second drain port in the second cultivation compartment is adapted to be fluidically connected with a third cultivation compartment upon opening of a second valve means of the second drain port to transfer the content of the second cultivation compartment to the third cultivation compartment upon completion of a second cell cultivation stage to leave the second cultivation compartment empty and wherein said third cultivation compartment has a volume of at least 150% of the volume of the second cultivation compartment,
wherein said drain ports are closed during each stage of cell cultivation,
wherein each cultivation compartment comprises a top film and a bottom delimiting film, delimiting one temperature control compartment from said each cultivation compartment, and
wherein said valve means is a pinch valve or a pinch clamp adapted for application on tubing or conduits of up to 15 mm outer diameter.

* * * * *